(12) United States Patent
Miller et al.

(10) Patent No.: US 7,544,645 B2
(45) Date of Patent: Jun. 9, 2009

(54) TRIESTER-BASED LUBRICANTS AND METHODS OF MAKING SAME

(75) Inventors: Stephen Joseph Miller, San Francisco, CA (US); Saleh A. Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 317 days.

(21) Appl. No.: 11/696,564

(22) Filed: Apr. 4, 2007

(65) Prior Publication Data

US 2008/0248982 A1    Oct. 9, 2008

(51) Int. Cl.
*C10M 105/38* (2006.01)
(52) U.S. Cl. ..................................... 508/485
(58) Field of Classification Search ................... 508/485
See application file for complete search history.

(56) References Cited

U.S. PATENT DOCUMENTS 4,981,602 A     1/1991   Ripple et al.
5,064,546 A    11/1991   Dasai

OTHER PUBLICATIONS

Dmytryshyn et al., "Synthesis and characterization of vegetable oil derived esters: evaluation for their diesel additive properties," Bioresources Technology 92 (2004) 55-64.

*Primary Examiner*—Glenn A Caldarola
*Assistant Examiner*—Pamela Weiss
(74) *Attorney, Agent, or Firm*—Edward Mickelson (57) ABSTRACT

The present invention is generally directed to triester-based lubricant compositions. The present invention is also directed to methods of making these and other similar lubricant compositions. In some embodiments, the methods for making such triester-based lubricants utilize a biomass precursor and/or low value Fischer-Tropsch (FT) products (e.g., alcohols) so as to produce high value triester-based lubricants. In some embodiments, such triester-based lubricants are derived, at least in part, from FT alcohols and fatty acids. The fatty acids can be from a bio-based source (i.e., biomass, renewable source) or can be derived from FT alcohols via oxidation.

41 Claims, 5 Drawing Sheets

Step 101 - esterfying a mono-unsaturated fatty acid to form an unsaturated ester Step 102 - epoxidizing the unsaturated ester to form an epoxy-ester species Step 103 - opening the epoxide ring of the epoxy-ester species to form a dihydroxy ester Step 104 - esterifying the dihydroxy ester to form a triester species

Table 1

| | VI | VIS cSt (40 °C) | VIS cSt (100 °C) | Pour point | Cloud Point |
|---|---|---|---|---|---|
| 9,10-Bis-hexanoyloxy-octadecanoic acid hexyl ester | 139 | 13.92 | 3.54 | -66 | -48 |
| 9,10-Bis-decanoyloxy-octadecanoic acid decyl ester | 157 | 42.73 | 7.87 | -29 | -29 |
| 50/50 wt% mixture (1) (2) | 159 | 25.1 | 5.4 | -39 | -38 |

Fig. 4

Table 2

| | Oxidation Stability Hr/1L O$_2$ uptake |
|---|---|
| Group I Lubricants | 7.2 |
| Group III Lubricants | 41.2 |
| Cargill Agri-Pure 75, 85, 560 | 0.17, 0.3, 0.41 |
| 50/50 wt% mixture (1) (2) | 8.08 |

Fig. 5

TRIESTER-BASED LUBRICANTS AND METHODS OF MAKING SAME

FIELD OF THE INVENTION

This invention relates to ester-based lubricants, and specifically to triester-based lubricants, and methods of making them—particularly wherein they are made from at least one biologically-derived precursor and/or Fischer-Tropsch product(s).

BACKGROUND

Esters have been used as lubricating oils for over 50 years. They are used in a variety of applications ranging from jet engines to refrigeration. In fact, esters were the first synthetic crankcase motor oils in automotive applications. However, esters gave way to polyalphaolefins (PAOs) due to the lower cost of PAOs and their formulation similarities to mineral oils. In full synthetic motor oils, however, esters are almost always used in combination with PAOs to balance the effect on seals, additives solubility, volatility reduction, and energy efficiency improvement by enhanced lubricity.

Ester-based lubricants, in general, have excellent lubrication properties due to the polarity of the ester molecules of which they are comprised. The polar ester groups of such molecules adhere to positively-charged metal surfaces creating protective films which slow down the wear and tear of the metal surfaces. Such lubricants are less volatile than the traditional lubricants and tend to have much higher flash points and much lower vapor pressures. Ester lubricants are excellent solvents and dispersants, and can readily solvate and disperse the degradation by-products of oils. Therefore, they greatly reduce sludge buildup. While ester lubricants are stable to thermal and oxidative processes, the ester functionalities give microbes a handle to do their biodegrading more efficiently and more effectively than their mineral oil-based analogues. However, the preparation of esters is more involved and more costly than the preparation of their PAO counterparts.

In view of the foregoing, a simpler, more efficient method of generating ester-based would be extremely useful—particularly wherein such methods utilize renewable raw materials in combination with converting low value Fischer-Tropsch (FT) products to high value ester lubricants.

BRIEF DESCRIPTION OF THE INVENTION

The present invention is generally directed to triester-based lubricant compositions. The present invention is also directed to methods of making these and other similar lubricant compositions. In some embodiments, the methods for making such triester-based lubricants utilize a biomass precursor. In these or other embodiments, lubricant precursor species can also be sourced or derived from Fischer-Tropsch (FT) reaction products.

In some embodiments, the present invention is directed to a lubricant composition comprising a quantity of at least one triester species, the triester species having the following structure:

wherein $R_1$, $R_2$, $R_3$, and $R_4$ are the same or independently selected from $C_2$ to $C_{20}$ hydrocarbon groups, and wherein "n" is a number from 2 to 20.

In some embodiments, the kinematic viscosity of the above-described composition at a temperature of 100° C. is at least 3 centistokes. In some or other embodiments, said composition has a pour point of less than −20° C.

For the above-described composition, $R_1$ is typically selected to have a total carbon number of from at least about 6 to at most about 12, $R_3$ and $R_4$ are typically selected to have a combined carbon number from at least about 2 to at most about 40, $R_2$ is typically selected to have a carbon number from at least about 1 to at most about 20, and "n," as denoted in —$(CH_2)_n$— in the above structure, is typically an integer in the range of from at least about 5 to at most about 10. Typically, for the lubricant composition described above, the at least one triester species has a molecular mass that is from at least about 400 atomic mass units (a.m.u.) to at most about 1100 a.m.u. More typically, the at least one triester species has a molecular mass that is from at least about 450 a.m.u. to at most about 1000 a.m.u.

In some embodiments, the above-described composition comprises at least one triester species of the type 9,10-bis-alkanoyloxy-octadecanoic acid alkyl ester and/or isomers and mixtures thereof, where the alkyl is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, and octadecyl; and where the alkanoyloxy is selected from the group consisting of ethanoyloxy, propanoyoxy, butanoyloxy, pentanoyloxy, hexanoyloxy, heptanoyloxy, octanoyloxy, nonaoyloxy, decanoyloxy, undacanoyloxy, dodecanoyloxy, tridecanoyloxy, tetradecanoyloxy, pentadecanoyloxy, hexadeconoyloxy, and octadecanoyloxy, 9,10-bis-hexanoyloxy-octadecanoic acid hexyl ester and 9,10-bis-decanoyloxy-octadecanoic acid decyl ester are exemplary such triesters.

In some embodiments, the above-described composition comprises quantities of at least two different triester species. In some or other embodiments, said composition further comprises a base oil selected from the group consisting of Group I oils, Group II oils, Group III oils, and combinations thereof. Additionally or alternatively, in some embodiments, said composition further comprises one or more diester species.

In some embodiments, the present invention is directed to methods of making the above-described composition, such methods comprising the steps of: (a) esterifying a mono-unsaturated fatty acid having a carbon number of from 10 to 22 with an alcohol so as to form an unsaturated ester; (b) epoxidizing the unsaturated ester to form an epoxy-ester species comprising an epoxide ring; (c) opening the ring of the epoxy-ester species to form a dihydroxy ester; and (d) esterifying the dihydroxy ester with an esterifying species to form a triester species, wherein the esterifying species is selected from the group consisting of carboxylic acids, acyl halides, acyl anhydrides, and combinations thereof, and wherein the esterifying species have a carbon number of from 1 to 18. In some such embodiments, said method can yield a mixture of triester species within the resulting lubricant composition by utilizing, in one or both of steps (a) and (d), reagents that comprise a range of carbon number.

In some such above-described method embodiments, the step of esterifying the mono-unsaturated fatty acid with an alcohol involves an acid catalyst. In some or other embodiments, the step of esterifying the mono-unsaturated fatty acid with an alcohol involves conversion of the fatty acid to an acyl halide or acyl anhydride species.

In some embodiments, such above-described methods further comprise a step of blending the triester species with other triester species. In some or other embodiments, such methods can further comprise a step of blending the triester species with one or more diester species. In some or still other embodiments, such methods can further comprise a step of blending the triester species with a base oil selected from the group consisting of Group I oils, Group II oils, Group III oils, and combinations thereof.

In some particular embodiments, wherein the above-described method uses oleic acid for the mono-unsaturated fatty acid, the resulting triester is of the type:

wherein $R_2$, $R_3$ and $R_4$ are typically the same or independently selected from $C_2$ to $C_{20}$ hydrocarbon groups, and are more typically selected from $C_4$ to $C_{12}$ hydrocarbon groups.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

1. INTRODUCTION

The present invention is directed to triester-based lubricant compositions. The present invention is also directed to methods of making these and other similar lubricant compositions. In some embodiments, the methods for making such triester-based lubricants utilize a biomass precursor and/or low value Fischer-Tropsch (FT) alcohols so as to produce high value triester-based lubricants. In these or other embodiments, the fatty (carboxylic) acids utilized in the synthesis can be from a bio-based source (i.e., biomass, renewable source) and/or they can be derived from FT alcohols via oxidation.

Because biolubricants and biofuels are increasingly gaining ground and becoming topics of focus for many in the oil industry, the use of biomass in the making of such above-mentioned lubricants could be attractive from several different perspectives. To the extent that biomass is so utilized in making the triester-based lubricants of the present invention, such lubricants are deemed to be biolubricants.

2. DEFINITIONS

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See American Petroleum Institute (API) Publication Number 1509.

"Cloud point," as defined herein, represents the temperature at which a fluid begins to phase separate due to crystal formation. See, e.g., ASTM Standard Test Methods D 5773-95, D 2500, D 5551, and D 5771.

"Centistoke," abbreviated "cSt," is a unit for kinematic viscosity of a fluid (e.g., a lubricant), wherein 1 centistoke equals 1 millimeter squared per second (1 cSt=1 mm$^2$/s). See, e.g. ASTM Standard Guide and Test Methods D 2270-04, D 445-06, D 6074, and D 2983.

With respect to describing molecules and/or molecular fragments herein, "$R_m$," where "m" is merely an identifier, refers to a hydrocarbon group, wherein the molecules and/or molecular fragments can be linear and/or branched, and unless stated otherwise, groups identified by different "m" identifiers can be the same or different.

As defined herein, "carbon number," as it relates to a hydrocarbon molecule or fragment (e.g., an alkyl group), is an integer denoting the total number of carbon atoms in the fragment or molecule. Carbon number with such a fragment or molecule can also be denoted as "$C_n$", where "n" is the total number of carbon atoms within that particular fragment or molecule.

The prefix "bio," as used herein, refers to an association with a renewable resource of biological origin, such as resource generally being exclusive of fossil fuels.

"Fischer-Tropsch products," as defined herein, refer to molecular species derived from a catalytically-driven reaction between CO and H$_2$ (i.e., "syngas").

3. TRIESTER LUBRICANT COMPOSITIONS

In some embodiments, the present, invention is generally directed to triester-based lubricant compositions comprising a quantity of triester species having the following chemical structure:

wherein $R_1$, $R_2$, $R_3$, and $R_4$ are the same or independently selected from. $C_2$ to $C_{20}$ hydrocarbon groups (groups with a carbon number from 2 to 20), and wherein "n" is an integer from 2 to 20.

Regarding the above-mentioned triester species, selection of $R_1$, $R_2$, $R_3$, $R_4$, and n can follow any or all of several criteria. For example, in some embodiments, $R_1$, $R_2$, $R_3$, $R_4$ and n are selected such that the kinematic viscosity of the composition at a temperature of 100° C. is typically 3 centistokes or greater. In some or other embodiments, $R_1$, $R_2$, $R_3$, $R_4$ and n are selected such that the pour point of the resulting lubricant is −20° C. or lower. In some embodiments, $R_1$ is selected to have a total carbon number of from 6 to 12. In these or other embodiments, $R_2$ is selected to have a carbon number of from 1 to 20. In these or other embodiments, $R_3$ and $R_4$ are selected to have a combined carbon number of from 4 to 36. In these or other embodiments, n is selected to be an integer from 5 to 10. Depending on the embodiment, such resulting triester species can typically have a molecular mass between 400 atomic mass units (a.m.u.) and 1100 a.m.u, and more typically between 450 a.m.u. and 1000 a.m.u.

In some embodiments, such above-described compositions are substantially homogeneous in terms of their triester component. In some or other embodiments, the triester component of such compositions comprises a variety (i.e., a mixture) of such triester species. In these or other embodiments, such above-described lubricant compositions further comprise one or more diester species.

In some of the above-described embodiments, the triester-based lubricant composition comprises one or more triester species of the type 9,10-bis-alkanoyloxy-oetadecanoic acid alkyl ester and isomers and mixtures thereof, where the alkyl is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, and octadecyl; and where the alkanoyloxy is selected from the group consisting of ethanoyloxy, propanoyoxy, butanoyloxy, pentanoyloxy, hexanoyloxy, heptanoyloxy, octanoyloxy, nonaoyloxy, decanoyloxy, undacanoyloxy, dodecanoyloxy, tridecanoyloxy, tetradecanoyloxy, pentaclecanoyloxy, hexadeconoyloxy, and octadecanoyloxy, 9,10-bis-hexanoyloxy-octadecanoic acid hexyl ester and 9,10-bis-decanoyloxy-octadecanoic acid decyl ester are exemplary such triesters. In some embodiments, the triester-based lubricant composition further comprises a base oil selected from the group consisting of Group I oils. Group II oils, Group III oils, and mixtures thereof.

It is worth noting that in most applications, the above-described triesters and their compositions are unlikely to be used as lubricants by themselves, but are usually used as blending stocks. As such, esters with higher pour points may also be used as blending stocks with other lubricant oils since they are very soluble in hydrocarbons and hydrocarbon-based oils.

4. METHODS OF MAKING TRIESTER LUBRICANTS

As mentioned above, the present invention is additionally directed to methods of making the above-described lubricant compositions and/or the triester compositions contained therein.

Figure 1:
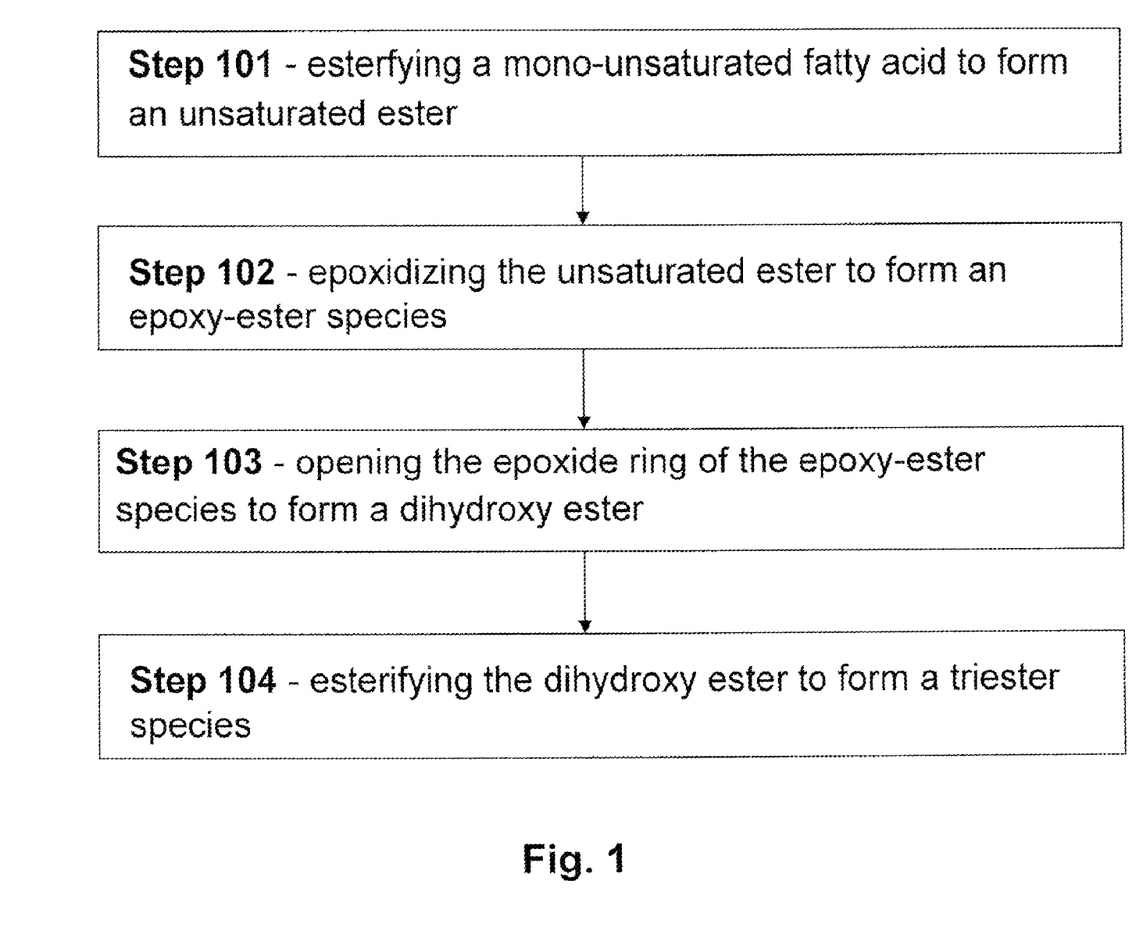
FIG. 1 is a flow diagram illustrating a method of making triester-based lubricant compositions, in accordance with some embodiments of the present invention.

Referring to the flow diagram shown in FIG. 1, in some embodiments, processes for making the above-mentioned triester-based compositions, typically having lubricating base oil viscosity and pour point, comprise the following steps: (Step 101) esterifying (i.e., subjecting to esterification) a mono-unsaturated fatty acid (or quantity of mono-unsaturated fatty acids) having a carbon number of from 16 to 22 with an alcohol to form an unsaturated ester (or a quantity thereof); (Step 102) epoxidizing the unsaturated ester to form an epoxy-ester species comprising an epoxide ring; (Step 103) opening the epoxide ring of the epoxy-ester species to form a dihydroxy-ester: and (Step 104) esterifying the dihydroxy-ester with an esterifying species to form a triester species, wherein such esterifying species are selected from the group consisting of carboxylic acids, acyl halides, acyl anhydrides, and combinations thereof; and wherein such esterifying species have a carbon number of from 2 to 18. Generally, lubricant compositions made by such methods and comprising such triester species have a viscosity of 3 centistokes or more at a temperature of 100° C. and they typically have a pour point of less than −20° C., and selection of reagents and/or mixture components is typically made with this objective.

In some embodiments, where a quantity of such triester species is formed, the quantity of triester species can be substantially homogeneous, or it can be a mixture of two or more different such triester species. In any such embodiments, such triester compositions can be further mixed with one or more base oils of the type Group I-III. Additionally or alternatively, in some embodiments, such methods further comprise a step of blending the triester composition(s) with one or more diester species.

In some embodiments, such methods produce compositions comprising at least one triester species of the type 9,10-bis-alkanoyloxy-octadecanoic acid alkyl ester and isomers and mixtures thereof where the alkyl is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, and octadecyl; and where the alkanoyloxy is selected from the group consisting of ethanoyloxy, propanoyoxy, butanoyloxy, pentanoyloxy, hexanoyloxy, heptanoyloxy, octanoyloxy, nonaoyloxy, decanoyloxy, undacanoyloxy, dodecanoyloxy, tridecanoyloxy, tetradecanoyloxy, pentadecanoyloxy, hexadeconoyloxy, and octadecanoyloxy. Exemplary such triesters include, but not limited to, 9,10-bis-hexanoyloxy-octadecanoic acid hexyl ester; 9,10-bis-octanoyloxy-octadecanoic acid hexyl ester; 9,10-bis-decanoyloxy-octadecanoic acid hexyl ester; 9,10-bis-dodecanoyoxy-octadecanoic acid hexyl ester; 9,10-bis-hexanoyloxy-octadecanoic acid decyl ester; 9,10-bis-decanoyloxy-octadecanoic acid decyl ester; 9,10-bis-octanoyloxy-octadecanoic acid decyl ester; 9,10-bis-dodecanoyloxy-octadecanoic acid decyl ester; 9,10-bishexanoyloxy-octadecanoic acid octyl ester; 9,10-bis-octanoyloxy-octadecanoic acid octyl ester: 9,10-bis-decanoyloxy-octadecanoic acid octyl ester; 9,10-bis-dodecanoyloxy-octadecanoic acid octyl ester; 9,10-bis-hexanoyloxy-octadecanoic acid dodecyl ester; 9,10-bis-octanoyloxy-octadecanoic acid dodecyl ester; 9,10-bis-decanoyloxy-octadecanoic acid dodecyl ester; 9,10-bis-doclecanoyloxy-octadecanoic acid dodecyl ester; and mixtures thereof.

In some such above-described method embodiments, the mono-unsaturated fatty acid can be a bio-derived fatty acid. In some or other such above-described method embodiments, the alcohol(s) can be FT-produced alcohols.

In some such above-described method embodiments, the step of esterifying (i.e., esterification) the mono-unsaturated fatty acid can proceed via an acid-catalyzed reaction with an alcohol using, e.g., $H_2SO_4$ as a catalyst. In some or other embodiments, the esterifying can proceed through a conversion of the fatty acid(s) to an acyl halide (chloride, bromide, or iodide) or acyl anhydride, followed by reaction with an alcohol.

Regarding the step of epoxidizing (i.e., the epoxidation step), in some embodiments, the above-described mono-unsaturated ester can be reacted with a peroxide (e.g., $H_2O_2$) or a peroxy acid (e.g., peroxyacetic acid) to generate an epoxy-ester species. See, e.g., D. Swern, in *Organic Peroxides Vol. II*, Wiley-Interscience, New York, 1971, pp. 355-533; and B. Plesnicar, in Oxidation in *Organic Chemistry, Part C*, W. Trahanovsky (ed.), Academic Press, New York 1978, pp. 221-253. Additionally or alternatively, the olefinic portion of the mono-unsaturated ester can be efficiently transformed to the corresponding dihydroxy ester by highly selective reagents such as osmium tetra-oxide (M. Schroder, Chem. Rev. vol. 80, p. 187, 1980) and potassium permanganate (Sheldon and Kochi, in *Metal-Catalyzed Oxidation of Organic Compounds*, pp. 162-171 and 294-296, Academic Press, New York, 1981).

Regarding the step of epoxide ring opening to the corresponding dihydroxy-ester, this step is usually an acid-catalyzed hydrolysis. Exemplary acid catalysts include, but are not limited to, mineral-based Brönsted acids (e.g., HCl, $H_2SO_4$, $H_3PO_4$, perhalogenates, etc.), Lewis acids (e.g., $TiCl_4$ and $AlCl_3$), solid acids such as acidic aluminas and silicas or their mixtures, and the like. See, e.g., Chem. Rev. vol. 59, p. 737, 1959; and Angew. Chem. Int. Ed., vol. 31, p. 1179, 1992. The epoxide ring opening to the diol can also be accomplished by base-catalyzed hydrolysis using aqueous solutions of KOH or NaOH.

Regarding the step of esterifying the dihydroxy-ester to form a triester, an acid is typically used to catalyze the reaction between the —OH groups of the diol and the carboxylic acid(s). Suitable acids include, but are not limited to, sulfuric acid (Munch-Peterson, Org. Synth., V, p. 762, 1973), sulfonic acid (Allen and Sprangler, Org Synth., III, p. 203, 1955), hydrochloric acid (Eliel et al., Org Synth., IV, p. 169, 1963), and phosphoric acid (among others). In some embodiments, the carboxylic acid used in this step is first converted to an acyl chloride (or another acyl halide) via, e.g., thionyl chloride or $PCl_3$. Alternatively, an acyl chloride (or other acyl halide) could be employed directly. Where an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. See, e.g., Fersh et al., J. Am. Chem. Soc., vol. 92, pp. 5432-5442, 1970; and Hofle et al., Angew. Chem. Int. Ed. Engl., vol. 17, p. 569, 1978. Additionally or alternatively, the carboxylic acid could be converted into an acyl anhydride and/or such species could be employed directly.

Regardless of the source of the mono-unsaturated fatty acid, in some embodiments, the carboxylic acids (or their acyl derivatives) used in the above-described methods are derived from biomass. In some such embodiments, this involves the extraction of some oil (e.g., triglyceride) component from the biomass and hydrolysis of the triglycerides of which the oil component is comprised so as to form free carboxylic acids.

Figure 2:
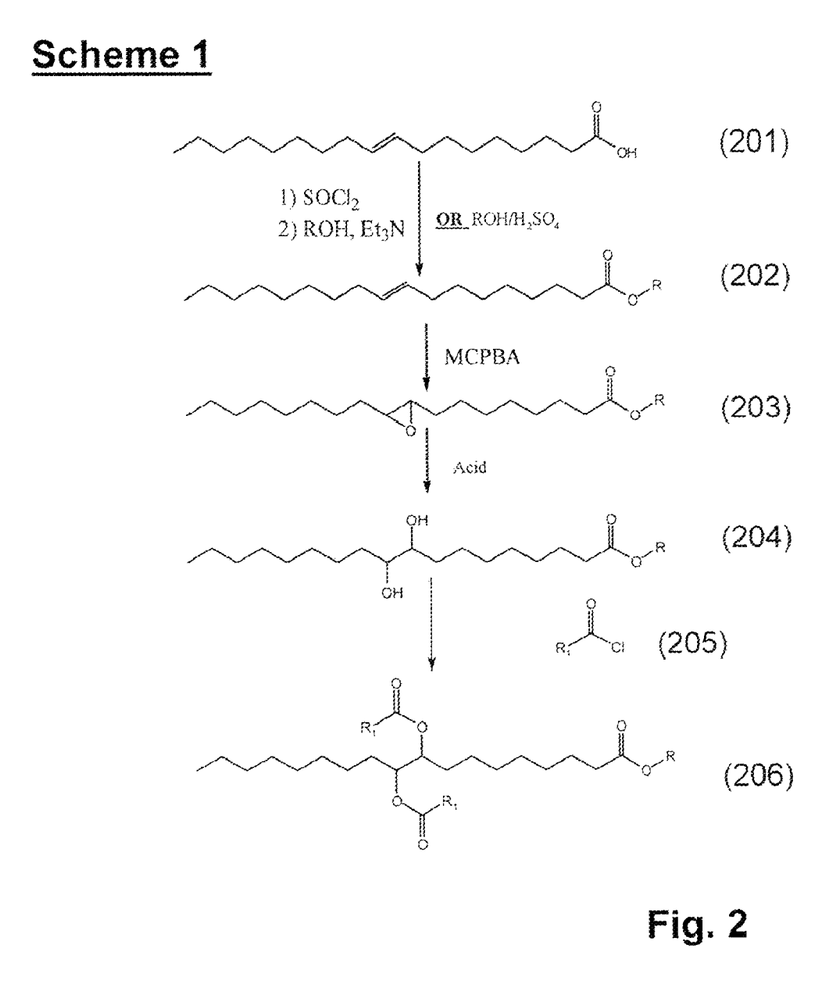
FIG. 2 (Scheme 1) is a chemical flow diagram illustrating an exemplary method of making a triester-based lubricant composition, in accordance with some embodiments of the present invention.
Figure 3:
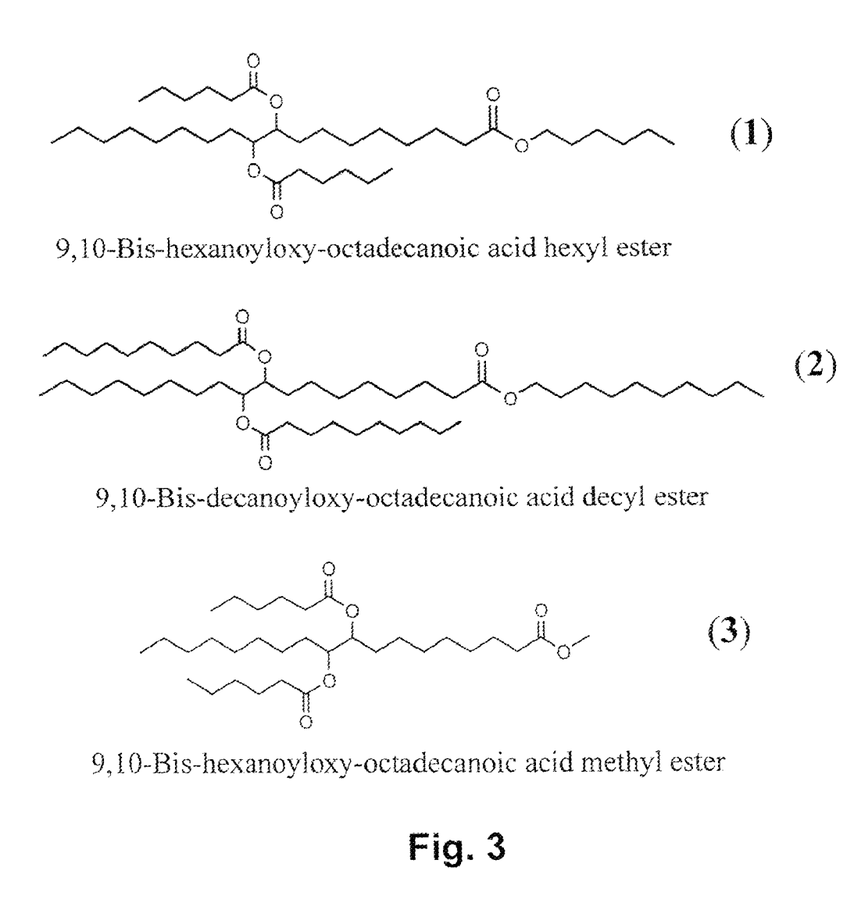
FIG. 3 depicts three exemplary triester-based compounds 1-3, suitable for use as lubricants in accordance with some embodiments of the present invention.

Using a synthetic strategy in accordance with that outlined in Scheme 1 (FIG. 2), oleic acid was converted to triester derivatives 1 (9,10-bis-hexanoyloxy-octadecanoic acid hexyl ester) and 2 (9,10-bis-decanoyloxy-octadecanoic acid decyl ester), shown in FIG. 3. Referring to FIG. 2, Scheme 1, oleic acid (201) is esterified to yield mono-unsaturated ester (202). Mono-unsaturated ester 202 is subjected to an epoxidation agent to give epoxy-ester species 203. The epoxy-ester species 203 undergoes ring-opening to yield dihydroxy ester 204, which can then be reacted with acyl chloride (205) to yield triester product 206.

The strategy of the above-described synthesis utilizes the double bond functionality in oleic acid by converting it to the diol via double bond epoxidation followed by epoxide ring opening. Accordingly, the synthesis begins by converting oleic acid to the appropriate alkyl oleate followed by epoxidation and epoxide ring opening to the corresponding diol derivative (dihydroxy ester). Triesters 1-3 were made using synthetic procedures described more fully in Examples 1-7 (vide infra). Triester 1 was made from oleic acid, hexyl alcohol and hexanoyl chloride. Triester 2 was derived from oleic acid, decyl alcohol and decanoyl chloride. Triester 3 was derived from oleic acid, methyl alcohol and hexanoyl chloride.

5. VARIATIONS

Variations on the above-described methods include, but are not limited to, generating (and utilizing) compositional ranges of triesters by blending and/or by compositional variation in the reagents used during the synthesis of the triester species described herein. Compositions produced by such method variations will, naturally, be variations themselves. All such variations fall within the scope of the compositions and methods described herein.

6. EXAMPLES

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

As an exemplary synthetic procedure, the synthesis of triester 1 (FIG. 3) is described in Examples 1-5. This procedure is representative for making triesters from mono-unsaturated carboxylic acids and alcohols, in accordance with some embodiments of the present invention.

Example 1

This Example serves to illustrate synthesis of an unsaturated acyl chloride (oleic acid chloride) en route to synthesis of a triester species, in accordance with some embodiments of the present invention (see, e.g., FIG. 2, Scheme 1). Oleic acid chloride was prepared according to the following procedure.

A three-neck 2-liter (L) round bottom reaction flask was fitted with a mechanical stirrer, reflux condenser and a water-filled trap to catch the evolving $SO_2$ and HCl gases. The flask was charged with 500 mL dichloromethane and 168 grams (0.14 mol) thionyl chloride. The reaction was cooled to 0° C. by means of an ice bath, and 200 grams (0.71 mol) of oleic acid was added drop-wise to the reaction vessel via an addition funnel. Once all of the oleic acid was added, the ice bath was replaced with a heating mantle and the reaction mixture was refluxed until the evolution of gases was ceased. The reaction mixture was cooled and concentrated on a rotary evaporator under reduced pressure to remove the solvent (dichloromethane) and excess thionyl chloride. The reaction afforded the desired oleoyl chloride as viscous oil in ~98% yield (210 g). The product identity was confirmed with nuclear magnetic resonance (NMR) and infrared (IR) spectroscopies, as well as gas chromatography/mass spectrometry (GC/MS).

Example 2

This Example serves to illustrate the synthesis of a mono-unsaturated ester from an unsaturated acyl chloride en route to synthesis of a triester species, in accordance with some embodiments of the present invention. Hexyl oleate was prepared from oleoyl chloride and hexanol in the presence of trimethyl amine according to the procedure below.

In a 3-neck 2-L reaction flask equipped with a mechanical stirrer, dropping funnel and a reflux condenser, 100 grams (0.33 mol) of oleoyl chloride (synthesized according to the procedure described in Example 1 above) were added drop-wise to a solution of 51 grams (0.5 mol) hexanol and 42 grams (0.41 mol) triethylamine at 0° C. in 800 mL anhydrous hexanes. Once the addition was complete, the reaction mixture was heated to reflux overnight. The reaction mixture was cooled down and neutralized with water. The two-layer solution was transferred to a separatory funnel, and the organic layer was separated and washed a few times with water. The aqueous layer was extracted with 500 mL of ether, and the ether extract was added to the organic layer and dried over $MgSO_4$. Filtration and concentration at reduced pressure gave the desired hexyl oleate mixed with excess hexanol. The products were purified by column chromatography by eluting first with hexanes and then with 3% ethyl acetate in hexane. The product was isolated as a pale yellow oil with a sweet ester odor. The product identity was confirmed with NMR and IR spectroscopies, as well as GC/MS. The reaction afforded a 93% yield (112 grams) of hexyl oleate.

Example 3

This Example serves to illustrate synthesis of an epoxy-ester species, in accordance with some embodiments of the present invention.

Epoxy-hexyl oleate [8-(3-octyl-oxiranyl)-octanoic hexyl ester] was made by epoxidation of the carbon-carbon double of hexyl oleate (synthesized according to the procedure described in Example 2 above) using meta-chloroperbenzoic acid (mCPBA) as the epoxidation agent. The synthesis is as follows.

A 1-L round bottom 3-neck reaction flask was equipped with a mechanical stirrer, powder funnel, and a reflux condenser. The flask was charged with 500 mL of dichloromethane and 110 grams (0.3 mol) hexyl oleate. The solution was cooled to 0° C., and 1101 grams of 77% meta-chloroperoxybenzoic acid (0.45 mol mCPBA) was added in small portions over a period of about 30 minutes. Once all of the mCPBA was added, the reaction was allowed to stir for 48 hours at room temperature. The resulting milky reaction solution was filtered, and the filtrate was washed twice with the slow addition of a 10% aqueous solution of sodium bicarbonate. The organic layer was washed several times with water, dried over anhydrous $MgSO_4$, and filtered. The filtrate was evaporated to give a waxy looking substance. NMR, IR and GC/MS analysis confirmed the authenticity of the product. The reaction yielded 93 grams (81%) that was fairly pure by GC/MS analysis.

Example 4

This Example serves to illustrate synthesis of a dihydroxy ester species, in accordance with some embodiments of the present invention.

Epoxide ring opening to the corresponding 9,10-dihydroxy-octadecanoic acid hexyl ester was accomplished by stirring the epoxy-ester species synthesized in Example 3 in a 3 wt % aqueous solution of perchloric acid ($HClO_4$) as follows.

In a 1-L reaction flask equipped with an overhead stirrer, 90 grams (0.23 mol) of the epoxy-ester were suspended in 300 mL of 3 wt % aqueous solution of perchloric acid and 300 mL hexane in a 2-L reaction flask. The suspension was vigorously stirred for 3 hours. The two-layer solution was separated and the aqueous layer was extracted with 300 mL ethyl acetate. The organic phases were combined and dried over $MgSO_4$. Filtration and concentration at reduced pressure on a rotary evaporator produced a viscous oil. Upon standing at room temperature, the oil separated into an oily phase and a white precipitate. The solids were separated from the oil by filtration. IR and GC/MS analysis showed the solid to be the desired dihydroxy ester species. The oily portion contained a number of unidentified products (diol- and hydroxyl-containing products, ester hydrolysis products, elimination products, and carbonyl-containing products). The reaction afforded approximately 52% (47 grams) of the desired 9,10-dihydroxy-octadecanoic acid hexyl ester.

Example 5

This Example serves to illustrate synthesis of a triester from a diol-ester, in accordance with some embodiments of the present invention.

Esterification of 9,10-dihydroxy-octadecanoic acid hexyl ester with hexanoyl chloride to 9,10-bishexanoyloxy-octadecanoic acid hexyl ester was accomplished by reacting the parent diol-ester with hexanoyl chloride (hexanoic acid chloride) in the presence of trimethyl amine in anhydrous hexanes according to the procedure below.

In a 1-L 3-neck reaction flask equipped with an overhead stirrer, reflux condenser, and a heating mantle, 45 grams (0.11 mol) of the dihydroxy ester (9,10-dihydroxy-octadecanoic acid hexyl ester, prepared according to the procedure of Example 4) and 33 grams of trimethyl amine (0.33 mol) were mixed in 250 mL anhydrous hexanes. To this mixture, 44 grams (0.33 mol) of hexanoyl chloride (Aldrich Chemical Co.) was added dropwise via an addition funnel over a 30-minute period. Once the addition was completed, the reaction was refluxed for 48 hours. The resulting milky solution was neutralized with water. The resulting two-phase solution was separated by means of a separatory funnel. The organic layer was washed extensively with water and the aqueous layer was extracted with 300 mL of ether. The organic layers were combined and dried over anhydrous $MgSO_4$, filtered, and concentrated at reduced pressure. GC/MS analysis of the resulting diester indicated the presence of hexanoic acid. The product was then washed with an ice-cold sodium carbonate solution to remove the residual hexanoic acid. The solution was extracted with ethyl acetate which was dried over $Na_2SO_4$, filtered, and concentrated to give the final desired triester (1) as a colorless oil in 83% yield (65 grams). The authentication of the final triester product was based on GC/MS, IR, and NMR analysis.

Example 6

This Example serves to illustrate the synthesis of 9,10-bis-decanoyloxy-octadecanoic acid decyl ester (2), in accordance with some embodiments of the present invention.

Decyl oleate was synthesized using the synthetic protocols described in Examples 1 and 2. The 9,10-dihydroxy-ocatanoic acid decyl ester was synthesized by epoxidizing decyl oleate according to the epoxidation procedure described in Example 3 followed by epoxide ring opening to the corresponding diol using the synthetic procedure described in Example 4. The triester, 9,10-bis-decanoyloxy-octadecanoic acid decyl ester, was synthesized by reacting 9,10-dihydroxy-ocatanoic acid decyl ester with decanoyl chloride (decanoic acid chloride) according to the procedure described in Example 5.

Example 7

This Example serves to illustrate the synthesis of 9,10-bis-hexanoyloxy-octadecanoic acid methyl ester (3), in accordance with some embodiments of the present invention.

9,10-bis-hexanoyloxy-octadecanoic acid methyl ester was synthesized using the same procedures described above from making 9,10-bis-hexanoyloxy-octadecanoic acid hexyl ester, but starting with methyl oleate instead of hexyl oleate. 9,10-bis-hexanoyloxy-octadecanoic acid methyl ester is a colorless oil with viscosity index (VI) of 110, viscosity of 12.9 at 40° C. and 3.18 at 100° C., pour point of −46° C., and cloud point of −33° C.

Example 8

This Example serves to illustrate a synthesis of 9,10-bis-decanoyloxy-octadecanoic acid hexyl ester, in accordance with some embodiments of the present invention.

To a solution of oleic acid (1 mole) and excess hexanol (2 mole equivalents), in a reaction flask equipped with a mechanical (overhead) stirrer and a reflux condenser, 10 mol % sulfuric acid is added and the mixture is heated at reflux. The reaction is driven to completion by removing water. Reaction progress is monitored by acid number determination. Once the reaction is finished, the mixture is cooled to room temperature and the reaction is worked up by washing with excess water and separating the oleic acid hexyl ester product from excess hexanol by distillation. Treating the resulting hexyl oleate according to the procedure described in Example 3 makes the epoxide ring [8-(3-octyl-oxyranyl-octadecanoic acid hexyl ester]. Subjecting the epoxide ring derivative to the synthetic procedure described in Example 4 produces the 9,10-dihydroxy-octadecanoic acid hexyl ester. To a mixture of the resulting diol (9,10-dihydroxy-octadecanoic acid hexyl ester) and excess decanoic acid (4 mole equivalents), 10 mol % sulfuric acid is added and the mixture is heated at reflux. The reaction is driven to completion by removing water azeotropically by introducing an azeotroping agent such as xylenes. Once the reaction is finished, the mixture is cooled down and washed with excess water. The triester 9,10-bis-decaoyloxy-octadecanoic acid hexyl ester product is separated from excess decanoic acid by distillation or by neutralizing the excess acid with one or more mild neutralizing agents like calcium hydride or sodium carbonate followed by filtration. The neutralized acid is recovered by acidification.

Example 9

This Example serves to illustrate the lubrication properties of some exemplary bioesters suitable for use as lubricants, in accordance with some embodiments of the present invention.

Figure 4:
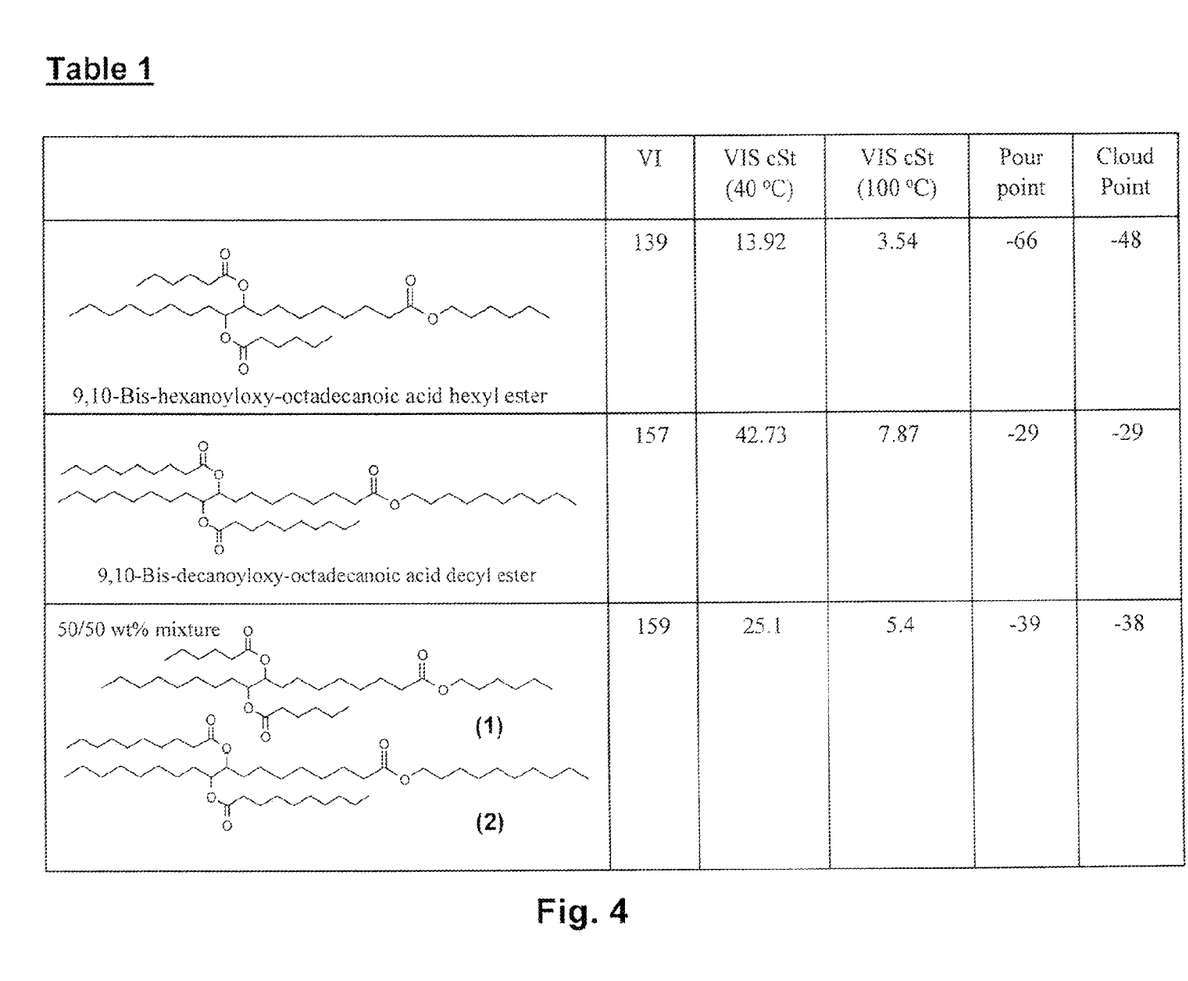
FIG. 4 (Table 1) compares lubrication properties of triester-based lubricants 1 and 2 and their mixture.

Esters 1 and 2 were prepared as described above and were tested and analyzed for several physical and lubricant properties including viscosity, viscosity index, cloud point, pour point and oxidation stability (see, e.g., ASTM Standard Test Method D 4636). These esters showed very promising lubricant properties. Table 1 (FIG. 4) summarizes the results of some of these tests and analyses.

Example 10

Figure 5:
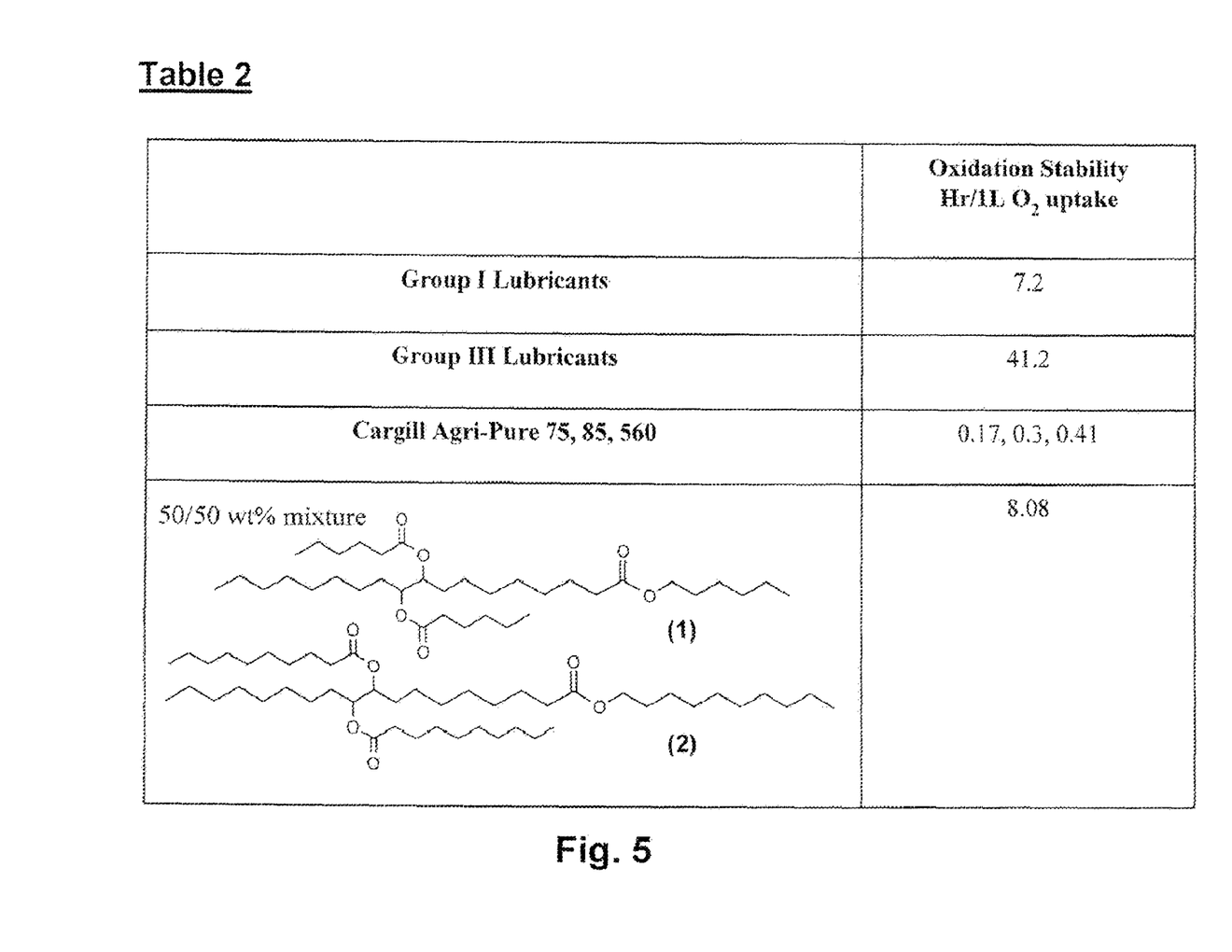
FIG. 5 (Table 2) compares oxidation stability of representative triester-based lubricants to that of other commercially-available lubricants.

This Example serves to illustrate the oxidation stability of some triester-based lubricant compositions and their comparison with other lubricant products. The associated data is shown in Table 2 (FIG. 5).

Referring to Table 2, the oxidation results for triesters 1 and 2 appear to resemble those of Group I oils. However, the oxidation stability of these triesters is superior to that of commercially-available bioesters. The Cargill Agri-Pure biolubricants 75 and 85 are high oleic canola oils, while Agri-Pure 560 is a synthetic polyol ester. In comparison to currently-available biolubricants, such triester compositions (e.g., 1 and 2) fare very well on all fronts: viscosity index (VI), viscosity (Vis), pour point, cloud point and oxidation stability. In fact, such triester compositions of the present invention are superior in their oxidation stabilities to the current market biolubes.

7. SUMMARY

In summary, the present invention provides for triester-based lubricant compositions. The present invention also provides for methods (processes) of making making these and other similar lubricant compositions. In some embodiments, the methods for making such triester-based lubricants utilize a biomass precursor and/or low value Fischer-Tropsch products so as to produce high value triester-based lubricants. In some embodiments, such triester-based lubricants are derived from FT alcohols and fatty acids. The fatty acids can be from a bio-based source (i.e., biomass, renewable source) or can be derived from FT alcohols via oxidation.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A lubricant composition comprising a quantity of at least one triester species, the triester species having the following structure:

wherein $R_1$, $R_2$, $R_3$, and $R_4$ are the same or independently selected from $C_2$ to $C_{20}$ hydrocarbon groups, and wherein n is an integer from 2 to 20.

2. The lubricant composition of claim 1, wherein the kinematic viscosity of the composition at a temperature of 100° C. is at least 3 centistokes.

3. The lubricant composition of claim 1, said composition having a pour point of less than −20° C.

4. The lubricant composition of claim 1, wherein $R_1$ is selected to have a carbon number from at least about 6 to at most about 12.

5. The lubricant composition of claim 1, wherein $R_3$ and $R_4$ are selected to have a combined carbon number from at least about 2 to at most about 40.

6. The lubricant composition of claim 1, wherein $R_2$ is selected to have a carbon number from at least about 1 to at most about 20.

7. The lubricant composition of claim 1, wherein n is an integer from 5 to 10.

8. The lubricant composition of claim 1, wherein said composition comprises quantities of at least two different triester species.

9. The lubricant composition of claim 1, wherein the at least one triester species has a molecular mass that is from at least about 400 a.m.u. to at most about 1100 a.m.u.

10. The lubricant composition of claim 1, wherein the at least one triester species is of a type selected from the group consisting of 9,10-bis-alkanoyloxy-octadecanoic acid alkyl ester and isomers thereof; and mixtures thereof; wherein the alkyl is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, and octadecyl; and wherein the alkanoyloxy is selected from the group consisting of ethanoyloxy, propanoyloxy, butanoyloxy, pentanoyloxy, hexanoyloxy, heptanoyloxy, octanoyloxy, nonaoyloxy, decanoyloxy, undacanoyloxy, dodecanoyloxy, tridecanoyloxy, tetradecanoyloxy, pentadecanoyloxy, hexadeconoyloxy, and octadecanoyloxy.

11. The lubricant composition of claim 1, wherein the at least one triester species is selected from the group consisting of 9,10-bis-hexanoyloxy-octadecanoic acid hexyl ester; 9,10-bis-octanoyloxy-octadecanoic acid hexyl ester; 9,10-bis-decanoyloxy-octadecanoic acid hexyl ester; 9,10-bis-dodecanoyloxy-octadecanoic acid hexyl ester; 9,10-bis-hexanoyloxy-octadecanoic acid decyl ester; 9,10-bis-decanoyloxy-octadecanoic acid decyl ester; 9,10-bis-octanoyloxy-octadecanoic acid decyl ester; 9,10-bis-dodecanoyloxy-octadecanoic acid decyl ester; 9,10-bis-hexanoyloxy-octadecanoic acid octyl ester; 9,10-bis-octanoyloxy-octadecanoic acid octyl ester; 9,10-bis-decanoyloxy-octadecanoic acid octyl ester; 9,10-bis-dodecanoyloxy-octadecanoic acid octyl ester; 9,10-bis-hexanoyloxy-octadecanoic acid dodecyl ester; 9,10-bis-octanoyloxy-octadecanoic acid dodecyl ester; 9,10-bis-decanoyloxy-octadecanoic acid dodecyl ester; 9,10-bis-dodecanoyloxy-octadecanoic acid dodecyl ester; and mixtures thereof.

12. The lubricant composition of claim 1, further comprising a base oil selected from the group consisting of Group I oils, Group II oils, Group III oils, and combinations thereof.

13. The lubricant composition of claim 1, further comprising one or more diester species.

14. A method comprising the steps of:
a) esterifying a mono-unsaturated fatty acid having a carbon number of from 10 to 22 with an alcohol so as to form an unsaturated ester;
b) epoxidizing the unsaturated ester to form an epoxy-ester species comprising an epoxide ring;
c) opening the ring of the epoxy-ester species to form a dihydroxy ester; and
d) esterifying the dihydroxy ester with an esterifying species to form a triester species, wherein the esterifying species is selected from the group consisting of carboxylic acids, acyl halides, acyl anhydrides, and combinations thereof, and wherein the esterifying species have a carbon number of from 1 to 18.

15. The method of claim 14, wherein the step of esterifying the mono-unsaturated fatty acid with an alcohol involves an acid catalyst.

16. The method of claim 14, wherein the step of esterifying the mono-unsaturated fatty acid with an alcohol involves conversion of the fatty acid to an acyl halide species.

17. The method of claim 16, wherein the acyl halide species is selected from, the group consisting of acyl chlorides, acyl bromides, acyl iodides, and combinations thereof.

18. The method of claim 14, wherein the step of esterifying the mono-unsaturated fatty acid with an alcohol involves conversion of the fatty acid to an acyl anhydride species.

19. The method of claim 14, further comprising a step of blending the triester species with other triester species.

20. The method of claim 14, further comprising a step of blending the triester species with one or more diester species.

21. The method of claim 14, further comprising a step of blending the triester species with, a base oil selected from the group consisting of Group I oils, Group II oils, Group III oils, and combinations thereof.

22. The method of claim 14, wherein said method yields a mixture of triester species by utilizing, in one or both of steps (a) and (d), reagents that comprise a range of carbon number.

23. A lubricant composition comprising a quantity of at least one triester species, the triester species having the following structure:

wherein $R_2$, $R_3$, and $R_4$ are the same or independently selected from $C_2$ to $C_{20}$ hydrocarbon groups.

24. The lubricant composition of claim 23, wherein the kinematic viscosity of the composition at a temperature of 100° C. is at least 3 centistokes.

25. The lubricant composition of claim 23, said composition having a pour point of less than −20° C.

26. The lubricant composition of claim 23, wherein $R_3$ and $R_4$ are selected to have a combined carbon number from at least about 2 to at most about 40.

27. The lubricant composition of claim 23, wherein $R_2$ is selected to have a carbon number from at least about 1 to at most about 20.

28. The lubricant composition of claim 23, wherein $R_2$, $R_3$, and $R_4$ are the same or independently selected from $C_4$ to $C_{12}$ hydrocarbon groups.

29. The lubricant composition of claim 23, wherein said composition comprises quantities of at least two different triester species.

30. The lubricant composition of claim 23, wherein the at least one triester species has a molecular mass that is from at least about 450 a.m.u. to at most about 1000 a.m.u.

31. The lubricant composition of claim 23, further comprising a base oil selected from the group consisting of Group I oils, Group II oils, Group III oils, and combinations thereof.

32. The lubricant composition of claim 23, further comprising one or more diester species.

33. A method comprising the steps of:
   a) esterifying oleic acid with an alcohol so as to form an unsaturated ester;
   b) epoxidizing the unsaturated ester to form an epoxy-ester species comprising an epoxide ring;
   c) opening the ring of the epoxy-ester species to form a dihydroxy ester; and
   d) esterifying the dihydroxy ester with an esterifying species to form a triester species, wherein the esterifying species is selected from the group consisting of carboxylic acids, acyl halides, acyl anhydrides, and combinations thereof and wherein the esterifying species have a carbon number of from 1 to 18.

34. The method of claim 33, wherein the step of esterifying the oleic acid with an alcohol involves an acid catalyst.

35. The method of claim 33, wherein the step of esterifying the oleic acid with an alcohol involves conversion of the oleic acid to an acyl halide species.

36. The method of claim 35, wherein the acyl halide species is selected from the group consisting of acyl chlorides, acyl bromides, acyl iodides, and combinations thereof.

37. The method of claim 33, wherein the step of esterifying the oleic acid with an alcohol involves conversion of the oleic acid to an acyl anhydride species.

38. The method of claim 33, further comprising a step of blending the triester species with other triester species.

39. The method of claim 33, further comprising a step of blending the triester species with one or more diester species.

40. The method of claim 33, further comprising a step of blending the triester species with a base oil selected from the group consisting of Group I oils, Group II oils, Group III oils, and combinations thereof.

41. The method of claim 33, wherein said method yields a mixture of triester species by utilizing, in one or both of steps (a) and (d), reagents that comprise a range of carbon number.

* * * * *